(12) United States Patent
Troy et al.

(10) Patent No.: US 9,156,321 B2
(45) Date of Patent: Oct. 13, 2015

(54) ADAPTIVE MAGNETIC COUPLING SYSTEM

(71) Applicant: The Boeing Company, Chicago, IL (US)

(72) Inventors: James J. Troy, Issaquah, WA (US); Scott W. Lea, Renton, WA (US); Daniel James Wright, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/166,150

(22) Filed: Jan. 28, 2014

(65) Prior Publication Data

US 2014/0137673 A1     May 22, 2014

Related U.S. Application Data

(62) Division of application No. 13/313,267, filed on Dec. 7, 2011, now Pat. No. 8,678,121.

(51) Int. Cl.
*B60K 17/30*     (2006.01)
*B60D 1/42*     (2006.01)
(Continued)

(52) U.S. Cl.
CPC . *B60D 1/42* (2013.01); *B25J 5/007* (2013.01); *B62D 57/024* (2013.01); *B62D 63/04* (2013.01);
(Continued)

(58) Field of Classification Search
CPC ............... H01F 7/0242; G01N 2291/2634; G01N 2291/2636
USPC .......... 180/167, 65.1; 73/618, 620, 635, 866.5
See application file for complete search history.

(56) References Cited

U.S. PATENT DOCUMENTS 5,865,661 A    2/1999   Cyrus et al.
6,131,460 A * 10/2000   Brunty et al. ................ 73/634
(Continued)

FOREIGN PATENT DOCUMENTS

WO     2006034066 A2     3/2006

OTHER PUBLICATIONS

International Preliminary Report on Patentability, issued on Jun. 10, 2014 in International Application No. PCT/ US2012/059098, which is the foreign counterpart to parent U.S. Appl. No. 13/313,267.
(Continued)

*Primary Examiner* — John Walters
*Assistant Examiner* — Brian Swenson
(74) *Attorney, Agent, or Firm* — Ostrager Chong Flaherty & Broitman P.C.

(57) ABSTRACT

A system is disclosed comprising a tractor vehicle, at least one trailer vehicle and a skin between and in contact with the tractor and trailer vehicles. One of the tractor and trailer vehicles is disposed in a non-inverted position above the skin and the other is disposed in an inverted position below the skin. The trailer vehicle comprises one or more magnets, while the tractor vehicle comprises one or more magnets magnetically coupled to each opposing magnet on the trailer vehicle. For example, the tractor and trailer vehicles may have mutually opposing permanent magnets in one-to-one relationship. Alternatively, each permanent magnet on the trailer vehicle could be opposed by one or more electro-permanent magnets on the tractor vehicle. The magnetic coupling between the magnets on the tractor and trailer vehicles produces an attraction force. The system further comprises means for maintaining the attraction force within a range as the tractor and trailer vehicles move along a portion of the skin having a varying thickness.

17 Claims, 12 Drawing Sheets

(51) Int. Cl.

| | | |
|---|---|---|
| *B25J 5/00* | (2006.01) | |
| *B62D 57/024* | (2006.01) | |
| *B64F 5/00* | (2006.01) | |
| *G01N 29/22* | (2006.01) | |
| *G01N 29/24* | (2006.01) | |
| *G01N 29/265* | (2006.01) | |
| *B62D 63/04* | (2006.01) | |
| *G01D 11/30* | (2006.01) | |
| *H01F 7/02* | (2006.01) | |

(52) U.S. Cl.
CPC .............. *B64F 5/0045* (2013.01); *G01D 11/30* (2013.01); *G01N 29/225* (2013.01); *G01N 29/2493* (2013.01); *G01N 29/265* (2013.01); *H01F 7/0242* (2013.01); *G01N 2291/2634* (2013.01); *G01N 2291/2636* (2013.01)

(56) References Cited

U.S. PATENT DOCUMENTS

| | | |
|---|---|---|
| 6,722,202 B1 | 4/2004 | Kennedy et al. |
| 7,231,826 B2 | 6/2007 | Bossi et al. |
| 7,249,512 B2 | 7/2007 | Kennedy et al. |
| 7,263,889 B2 | 9/2007 | Kennedy et al. |
| 7,484,413 B2 | 2/2009 | Georgeson et al. |
| 7,868,721 B2 * | 1/2011 | Fullerton et al. .............. 335/284 |
| 7,934,575 B2 | 5/2011 | Waibel et al. |
| 2006/0055396 A1 | 3/2006 | Georgeson et al. |
| 2006/0162456 A1 | 7/2006 | Kennedy et al. |

OTHER PUBLICATIONS http://www.livenv.net/wallbots, Oct. 4, 2011.
International Search Report and Written Opinion dated Feb. 18, 2013, for Int'l Application No. PCT/US2012/059098, which claims priority to the instant application.

* cited by examiner

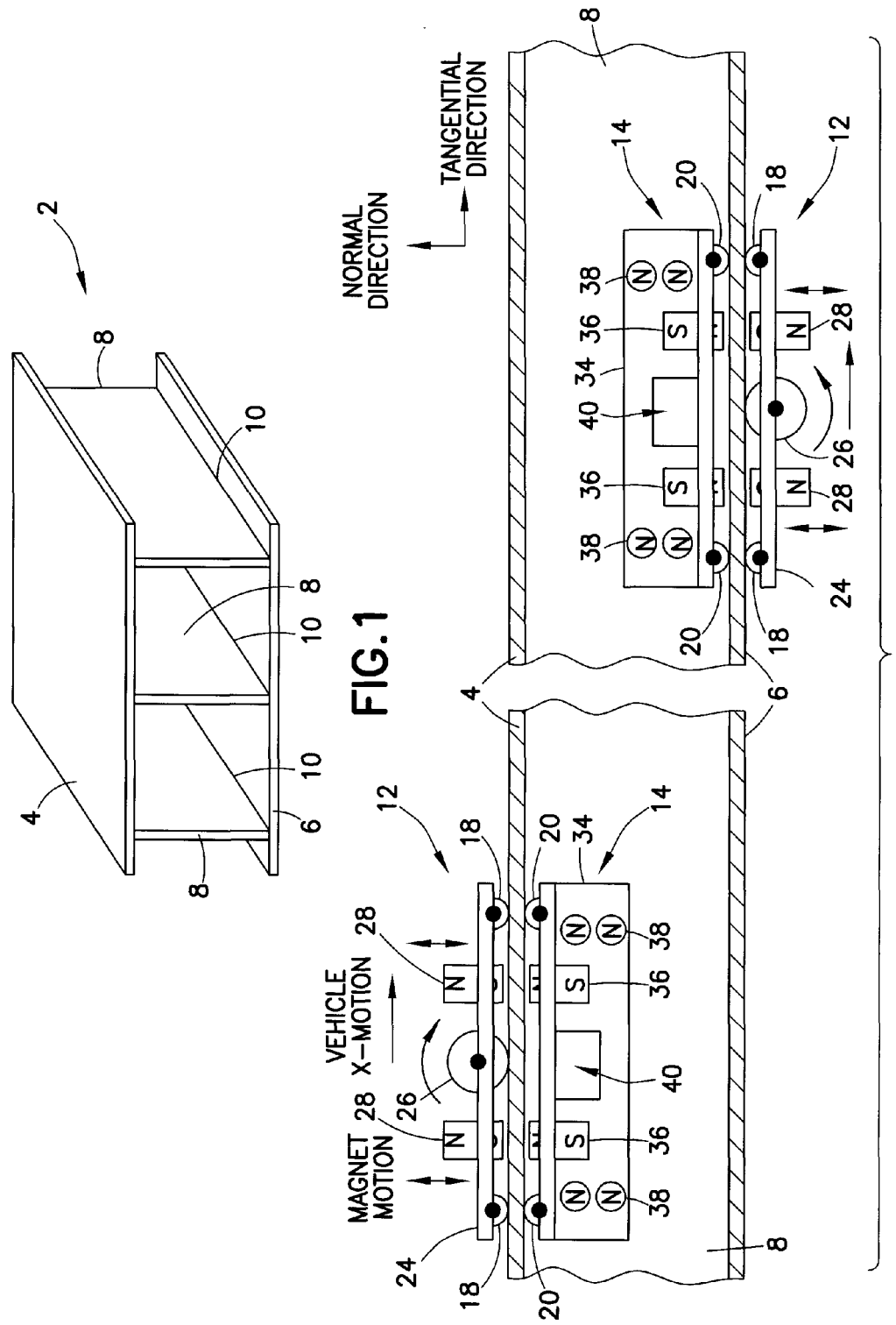

ADAPTIVE MAGNETIC COUPLING SYSTEM

RELATED PATENT APPLICATIONS

This application is a divisional of and claims priority from U.S. patent application Ser. No. 13/313,267 filed on Dec. 7, 2011, which in turn claims the benefit of and priority from U.S. Provisional Application No. 61/509,098 filed on Jul. 18, 2011.

BACKGROUND

This disclosure generally relates to systems for carrying payload across surfaces, such payload including (but not limited to) sensors used in nondestructive evaluation (NDE) and other types of tools. In particular, this disclosure relates to remotely operated systems for carrying tools, such as NDE sensors, through long tunnel-like passageways and areas with limited access.

Non-destructive inspection of structures involves thoroughly examining a structure without harming the structure or requiring significant disassembly of the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to the structure. Among the structures that are routinely non-destructively inspected are composite structures. As such, it is frequently desirable to inspect composite structures to identify any flaws, such as cracks, voids, or porosity, which could adversely affect the performance of the composite structure.

Various types of sensors may be utilized to perform non-destructive inspection. One or more sensors may move over the structure to be examined, and receive data regarding the structure from which internal flaws can be identified. The data acquired by the sensors is typically processed by a processing element, and the processed data may be presented to a user via a display.

Accessibility to the structural features requiring inspection is one consideration in choosing a non-destructive inspection device. Access to the structural feature requiring inspection may be so limited that a manual inspection by a technician is not possible. An example of a structure with limited access is an internal joint of a wing structure. More specifically, the bond lines produced by close-out joints, created when the last sections of the wing are attached, exemplify the limited-access features of a structure. Limited-access features of a structure, such as the close-out joints, are difficult to fully inspect.

Another example of a structure with limited access is the internal structure of an airplane composite horizontal stabilizer. Ultrasonic NDE sensors can be used to inspect horizontal stabilizer internal vertical support elements or webs, called "spars", and the filleted join regions between each spar and top and bottom skins. For this type of inspection, the NDE sensors need to be placed in contact with the surface in the region being inspected. One of the main challenges to performing the inspection is that the areas of interest must be inspected after the horizontal stabilizer has been constructed, which makes most of the areas to be inspected difficult to access.

Magnetic coupling systems for use in the inspection of features within a difficult-to-access space are known. One such system comprises a traction motor-powered "tractor" vehicle that rides on one surface of a skin or panel, which tractor is magnetically coupled to one or more passive "trailer" vehicles riding on another surface of the same skin or panel. The vehicle or vehicles riding on the opposing surface of the skin or panel may be inverted. With this type of magnetic coupling system, the tractor vehicle pulls the trailer vehicle(s) along the desired path.

In the foregoing known magnetic coupling system, the coupling magnets are arranged in multiple North-South pairs on the tractor and trailer vehicles, preferably close enough to each other to provide an attraction force equal to at least the weight of the inverted vehicle(s) plus a safety margin. Magnet pairs produce both normal and tangential (shear) forces between the inner and outer vehicles. These magnets do not touch the skin or panel, but instead are held at a constant distance from the surface which the respective vehicle is in contact with. The amount of separation between each pair of opposing poles of the coupling magnets determines the amount of attachment force in the direction normal to the surface and shear force in the tangential direction. Since the attraction force in magnetically coupled systems is inversely proportional to the square of the separation distance, a relatively small change in the distance between the magnet poles will produce a large change in the attraction force.

A problem arises when the thickness of the skin or panel to which the magnetic coupling system (including at least one inverted vehicle) is mounted varies considerably from one end of the structure to be inspected to the other. The magnetic force has to be enough to keep the inverted vehicle(s) in contact with the skin surface, but it should not be so large that too much friction and rolling resistance is developed for the drive motor to overcome. In addition, too much force on the wheels may damage the skin surface. In order to satisfy these constraints, the magnet separation distance needs to be set within a fairly tight tolerance.

There is a need for system that can actively control the attraction force between the coupling magnets as the vehicles move from one end of a structure to the other end, automatically adapting to the variable thickness of an intervening panel of that structure.

SUMMARY

The systems disclosed herein address the above needs and attain other advantages by providing a system that actively controls the attraction force between the coupling magnets as the vehicles move from one end of the structure to the other end, automatically adapting to the variable thickness of the intervening structure.

In an aircraft horizontal stabilizer made of composite material, for example, skin thickness varies considerably from one end of the structure to the other. A magnet separation setting that just barely keeps the inverted vehicle attached at the inboard (thicker) end of the horizontal stabilizer will generate too much force at the other (thinner) end, possibly damaging the composite material.

In order to address this problem, the system disclosed herein actively adjusts the magnitude of the attraction force between the magnets used to couple an active "tractor" vehicle to passive "trailer" vehicles. As the system moves over a variable-thickness skin, sensor data is used by a control system to determine the appropriate attraction force between the vehicles, enabling the magnetic coupling system to automatically adapt to the variable skin thickness.

In accordance with one aspect of the teachings herein, a system is provided which comprises a tractor vehicle, a trailer vehicle and a skin between and in contact with the tractor vehicle and the trailer vehicle, one of the tractor vehicle and the trailer vehicle being disposed in a non-inverted position above the skin and the other of the tractor vehicle and the trailer vehicle being disposed in an inverted position below the skin, wherein the trailer vehicle comprises one or more magnets (each with two magnetic poles), the tractor vehicle comprises a respective one or more magnets magnetically coupled to each opposing magnet pole on the trailer vehicle, and the magnetic coupling between the magnet poles on the tractor and trailer vehicles produces an attraction force, the system further comprising means for maintaining the attraction force within a range as the tractor vehicle and the trailer vehicle move along a portion of the skin having a varying thickness.

Another aspect is a system comprising a tractor vehicle, a trailer vehicle and a skin between and in contact with the tractor vehicle and the trailer vehicle, one of the tractor vehicle and the trailer vehicle being disposed in a non-inverted position above the skin and the other of the tractor vehicle and the trailer vehicle being disposed in an inverted position below the skin, wherein: the trailer vehicle comprises a frame and at least one magnet supported by the frame, and the tractor vehicle comprises a frame, a carriage slidably mounted to the frame, at least one magnet carried by the carriage, a transmission coupled to the carriage, and a motor for driving sliding displacement of the carriage via the transmission, the magnets being magnetically coupled to produce an attraction force, the system further comprising: a device for determining the current value of a variable that has a known relationship to the magnitude of the attraction force, and a controller programmed to control the motor to cause the carriage to displace by an amount that maintains the magnitude of the attraction force within a range, the amount of displacement being a function of the current value of the variable.

A further aspect is a method for magnetically coupling a pole of a first magnet onboard a tractor vehicle to a pole of a second magnet onboard a trailer vehicle through an intervening skin having a variable thickness along a vehicle travel path, comprising: placing one of the tractor vehicle and the trailer vehicle in a non-inverted position with wheels in contact with a top surface of the skin; placing the other of the tractor vehicle and the trailer vehicle in an inverted position with wheels in contact with a bottom surface of the skin and with the first and second magnets magnetically coupled to each other; driving the tractor vehicle along the vehicle travel path with the trailer vehicle magnetically coupled thereto; and adjusting the vertical position of the first magnet as the tractor vehicle travels along the vehicle travel path, the adjustments being selected to maintain an attraction force between the first and second magnets within a range as the skin thickness varies along the vehicle travel path.

Yet another aspect is a method for magnetically coupling an array of electro-permanent magnets onboard a tractor vehicle to a permanent magnet onboard a trailer vehicle through an intervening skin having a variable thickness along a vehicle travel path, comprising: placing one of the tractor vehicle and the trailer vehicle in a non-inverted position with wheels in contact with a top surface of the skin; placing the other of the tractor vehicle and the trailer vehicle in an inverted position with wheels in contact with a bottom surface of the skin and with a pole of the permanent magnet magnetically coupled to a pole of at least one electro-permanent magnet; driving the tractor vehicle along the vehicle travel path with the trailer vehicle magnetically coupled thereto; and adjusting the number of electro-permanent magnets of the array which are in an active state as the tractor vehicle travels along the vehicle travel path. The adjustments to the number of electro-permanent magnets in the array which are active maintain an attraction force within a range. as the skin thickness varies along the vehicle travel path.

A further aspect is a surface vehicle comprising: a frame; a plurality of wheels that are rotatable relative to the frame; a drive wheel that is rotatable relative to the frame; a first transmission coupled to the drive wheel; a first motor for driving rotation of the drive wheel via the first transmission; a carriage slidably mounted to the frame; a magnet carried by the carriage; a second transmission coupled to the carriage; and a second motor for driving sliding displacement of the carriage via the second transmission, the magnet being displaceable relative to the frame in response to actuation of the second motor.

Yet another aspect is a surface vehicle comprising: a frame; a plurality of wheels that are rotatable relative to the frame; a drive wheel that is rotatable relative to the frame; a transmission coupled to the drive wheel; a motor for driving rotation of the drive wheel via the transmission; an array of electro-permanent magnets mounted to the frame, and a reversible coil switching unit for selectively activating one or more electro-permanent magnets of the array in response to control signals.

Other aspects are disclosed below.

BRIEF DESCRIPTION OF THE DRAWINGS

FIG. 1 is a diagram showing an orthographic view of a portion of a generic horizontal stabilizer of an airplane having top and bottom skins or panels connected by a plurality of vertical walls or webs (hereinafter referred to as "spars" when discussing the inspection of horizontal stabilizers).

FIG. 2 is a diagram showing side views of a tractor-trailer configuration having means for adaptive magnetic coupling in accordance with one embodiment. A second trailer vehicle is not visible in FIG. 2. The left-hand side of FIG. 2 shows an inspection scenario wherein the trailer vehicles are inverted, while the right-hand side shows an inspection scenario wherein the tractor vehicle is inverted.

FIGS. 6 and 7 show the magnet carriage in extended and retracted positions respectively. Actuator motors are not shown.

FIG. 12 shows two pairs of magnets separated by a minimum lateral distance, whereas FIG. 13 shows the same magnet pairs separated by a maximum lateral distance.

Reference will hereinafter be made to the drawings in which similar elements in different drawings bear the same reference numerals.

DETAILED DESCRIPTION

Figure 3:
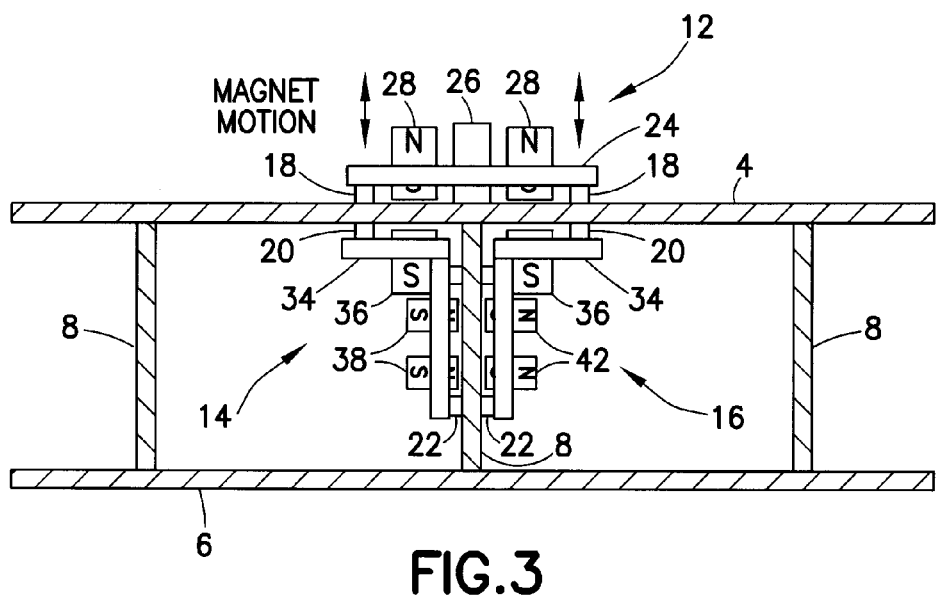
FIG. 3 is a diagram showing an end view of the tractor-trailer configuration depicted on the left-hand side of FIG. 2 (with respective inverted trailer vehicles disposed on both sides of a spar).

For the purpose of illustration, various embodiments of automated non-destructive inspection (NDI) vehicles capable of inspecting long tunnel-like passageways and areas with limited access (such as the interior of a horizontal stabilizer for an aircraft) will be described hereinafter. However, it should be appreciated that the teachings disclosed hereinafter have application in fields other than non-destructive inspection. In particular, magnetically coupled trailer vehicles of the types disclosed herein can carry cameras, tools, painting equipment, a laser marking system, a robotic arm manipulator, or other devices in limited-access spaces.

The broad concept disclosed herein involves adapting the attraction force between magnetically coupled tractor and trailer vehicles as the thickness of an intervening skin varies along the travel path of the coupled vehicles. This concept has been implemented in a system that comprises a tractor vehicle, a trailer vehicle and a skin between and in contact with the tractor vehicle and the trailer vehicle. One of the tractor and trailer vehicles is disposed in a non-inverted position above the skin and the other is disposed in an inverted position below the skin. The trailer vehicle comprises one or more magnets, while the tractor vehicle comprises a respective one or more magnets magnetically coupled to each magnet on the trailer vehicle. For example, the tractor and trailer vehicles may have mutually opposing permanent magnets in one-to-one relationship. Alternatively, each permanent magnet on the trailer vehicle could be opposed by one or more electro-permanent magnets instead of a single permanent magnet on the tractor vehicle. The magnetic coupling between the magnets on the tractor and trailer vehicles produces an attraction force. The system further comprises means for maintaining the attraction force within a range as the tractor and trailer vehicles move along a portion of the skin having a varying thickness. Specific embodiments will now be described, which embodiments were specifically designed for use in non-destructive inspection of a horizontal stabilizer made of composite material and other composite airplane components that have long tunnel-like passageways and areas with limited access (for example, the vertical stabilizer and main wings).

In accordance with one embodiment, ultrasonic NDI sensors are used to inspect a horizontal stabilizer. A portion of an idealized horizontal stabilizer 2 for an aircraft is depicted in FIG. 1. The depicted horizontal stabilizer comprises a top skin 4, a bottom skin 6 and a plurality of internal vertical support elements or webs 8 called "spars", which are joined to the top and bottom skins by filleted join regions 10 (only three of which are visible in FIG. 1). For this type of inspection, the NDI sensors are carried by a trailer vehicle (not shown in FIG. 1) placed inside the hollow structure seen in FIG. 1. The NDI sensors need to be acoustically coupled to the surface being inspected while an automated tractor vehicle (not shown in FIG. 1) moves the trailer vehicle along that surface in a region of interest.

FIG. 2 shows side views of a tractor-trailer configuration in two different inspection situations (motor actuators are not shown). The automated NDI inspection system comprises a traction-motor powered tractor vehicle 12, which rides on the external surface of top skin 4 or bottom skin 6 of horizontal stabilizer 2, and a pair of passive trailer vehicles (only trailer vehicle 14 is visible in FIG. 2, the other being hidden behind a spar 8), which ride along an internal surface of the top or bottom skin. The left-hand side of FIG. 2 shows an inspection scenario wherein the tractor vehicle 12 is outside the horizontal stabilizer in a non-inverted position while the trailer vehicles are inside the horizontal stabilizer in inverted positions; the right-hand side of FIG. 2 shows an inspection scenario wherein the tractor vehicle 12 is outside the horizontal stabilizer in an inverted position while the trailer vehicles are inside the horizontal stabilizer in non-inverted positions. FIG. 3 shows an end view of the tractor-trailer configuration depicted on the left-hand side of FIG. 2, with inverted trailer vehicles 14 and 16 disposed on opposite sides of spar 8.

In the inspection scenario depicted in FIG. 3 and the left-hand side of FIG. 2, idler wheels 18 of tractor vehicle 12 contact and roll on the external surface of top skin 4 while idler wheels 20 of inverted trailer vehicles 14 and 16 (only one such idler wheel is visible in FIG. 3 for each trailer vehicle) contact and roll on the internal surface of top skin 4. The right-hand side of FIG. 2 show an alternative situation wherein idler wheels 18 of the inverted tractor vehicle 12 contact and roll on the external surface of bottom skin 6 while idler wheels 20 of trailer vehicle 14 (and also idler wheels of trailer vehicle 16 not visible in FIG. 2) contact and roll on the internal surface of bottom skin 6.

In accordance with the embodiment partly depicted in FIGS. 2 and 3, the tractor vehicle 12 comprises a frame 24. Four idler wheels 18 (only two of which are visible in each of FIGS. 2 and 3) are rotatably mounted to frame 24 in a conventional manner. The idler wheels 18 are made of plastic and have smooth contact surfaces. Tractor vehicle motion is enabled by driving a drive wheel 26 (also rotatably mounted to frame 24) to rotate. As will be described in more detail later with reference to FIG. 9, drive wheel 26 is coupled to a motor 30 via a transmission 32. The drive wheel 26 is positioned on the frame 24 so that it is in frictional contact with skin 4 or 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 2 and 3, each trailer vehicle 14, 16 comprises a frame 34. For each trailer vehicle, two vertical idler wheels 20 (only one of which is visible in FIG. 3) and four horizontal idler wheels 22 (only two of which are visible in FIG. 3) are rotatably mounted to frame 34 in a conventional manner. The idler wheels 20 and 22 are made of plastic and have smooth contact surfaces. Idler wheels 20 bear against the internal surface of top skin 4 (see left-hand side of FIG. 2) or of bottom skin 6 (see right-hand side of FIG. 2). Idler wheels 22 of trailer vehicle 14 bear against one side of spar 8, while idler wheels 22 of trailer vehicle 16 bear against the other side of spar 8. In addition, each trailer vehicle 14, 16 carries multiple vertically mounted permanent magnets 36, the North poles of which are magnetically coupled to the South poles of confronting permanent magnets 28 carried by the tractor vehicle 12. (Alternatively, some or all of magnets 28 and 36 could be reversed so that the South poles of magnets 36 are magnetically coupled to the North poles of magnets 28.) In the design described by FIGS. 2 and 3, each trailer has two vertically mounted permanent magnets 36, but other designs may use different configurations.

As seen in FIG. 3, in addition to being magnetically coupled to the tractor vehicle 12, the trailer vehicles 14 and 16 are magnetically coupled to each other using additional sets of permanent magnets 38 and 42. As seen in FIG. 2, trailer vehicle 14 carries four horizontally mounted permanent magnets 38. Trailer vehicle 16 also carries four horizontally mounted permanent magnets 42 (only two of which are visible in FIG. 3), the poles of which are respectively magnetically coupled to opposing poles of the permanent magnets 38 on trailer vehicle 14. In the embodiment depicted in FIGS. 2 and 3, the North poles of permanent magnets 38 on trailer vehicle 14 are magnetically coupled to the South poles of permanent magnets 42 on trailer vehicle 16, producing an attraction force that holds idler wheels 22 of trailer vehicles 14 and 16 in contact with opposing surfaces of an intervening spar 8 (shown in FIG. 3).

As seen in FIG. 2, trailer vehicle 14 further carries a payload 40. For the NDI scenario depicted in FIGS. 2 and 3, payload 40 is an ultrasonic NDI sensor or sensor array which is acoustically coupled to the internal surface of spar 8 which idler wheels 22 of trailer vehicle 14 are in contact with. For example, the inspected region may be sprayed with water to acoustically couple the ultrasonic sensor(s) to the spar 8. Magnetically coupled systems are well suited for operation with water in the environment.

As the tractor vehicle is driven to travel along a desired path on the outer surface of the top or bottom skin, it pulls the inner trailer vehicles along. The magnetic coupling system described above keeps the inverted vehicle(s) in contact with the surface it rides on. For horizontal stabilizer applications, two magnetically coupled trailer vehicles can be used, one on each side of the spar 8, as shown in FIG. 3. This allows the system to take advantage of the internal structure of the scanned object as a guide to allow the system to track properly along the surface.

The system partly depicted in FIGS. 2 and 3 further comprises means (not shown in FIGS. 2 and 3) for automatically adapting to the variable thickness of the intervening skin or panel (i.e., top skin 4 or bottom skin 6) by raising or lowering the magnets (which magnet motion is indicated by double-headed arrows in FIG. 2) on the tractor vehicle as it moves along the structure being inspected. The amount of separation between each pair of opposing poles of the coupling magnets on the trailer and tractor vehicles determines the amount of attraction in the direction normal to the skin or panel and shear force in the tangential direction. A specific implementation of means for raising or lowering the tractor vehicle magnets in groups will be described later with reference to FIGS. 6 and 7. This magnet displacement feature enables the system to automatically compensate for changes in skin thickness that would otherwise cause undesirable changes in the attraction forces that couple the tractor/trailer vehicles.

Figure 4:
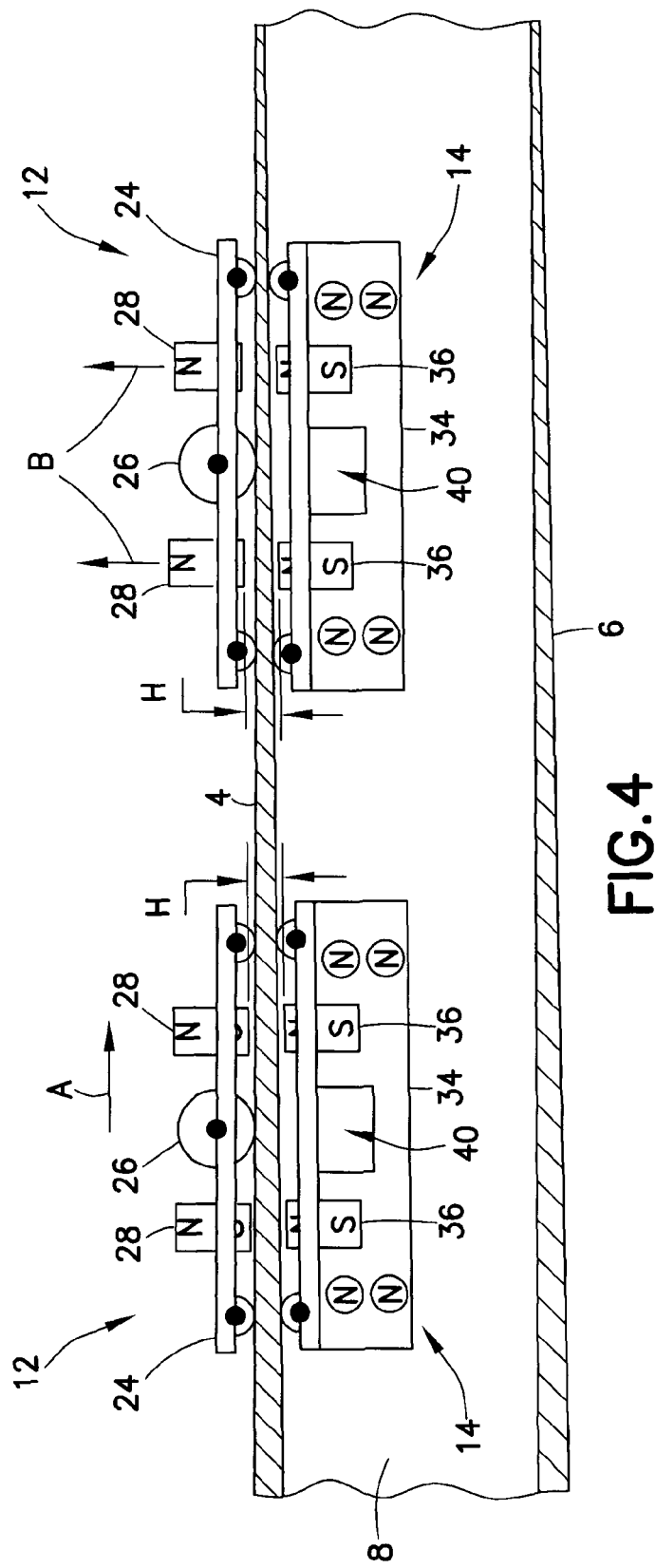
FIG. 4 is a diagram showing a side view of a tractor-trailer configuration having means for adjusting the vertical position of the tractor-mounted magnets as the tractor-trailer configuration moves from left to right along a top skin whose thickness decreases in the same direction.

FIG. 4 shows side views of the tractor-trailer configuration depicted in FIGS. 2 and 3 as it moves left to right along a top skin 4 whose thickness decreases in the same direction. As the tractor vehicle moves in the direction indicated by arrow A, respective pairs of magnets 28 are independently displaced upward relative to frame 24 of tractor vehicle 12, as indicated by arrows B in FIG. 4. In the position and state shown on the left side of FIG. 4, magnets 28 on tractor vehicle 12 are separated from the opposing magnets 36 on trailer vehicle 14 and the other trailer vehicle not visible in FIG. 4 by a distance ideally equal to H. Then the trailers move from left to right, during which travel time the vertical positions of magnets 28 on tractor vehicle 12 are adjusted (i.e., displaced upward) to compensate for decreases in skin thickness. The result is that in the position and state shown on the right side of FIG. 4, magnets 28 on tractor vehicle 12 are separated from magnets 36 on the trailer vehicles by the same distance H despite the change in skin thickness. The adjustments are computed using an algorithm that first determines the current value of a variable having a known relationship to the magnitude of the attraction force produced by a pair of mutually opposing magnets 28 and 36, and then determines the amount by which the tractor vehicle magnet 28 needs to be displaced in order to maintain the magnitude of the attraction force within a preset range. The same principle can be applied to groups of pairs of mutually opposing magnets. The permanent magnets 28 onboard the tractor vehicle 12 can be moved individually or in groups in dependence on the magnet separation distance. For example, the leading and trailing pairs of magnets 28 on the tractor vehicle 12 can be displaced vertically by different amounts to take into account the difference in skin thickness at the present location of the leading pair as compared to at the present location of the trailing pair of magnets.

FIGS. 2-4 show a tractor-trailer configuration in which the tractor vehicle carries four permanent magnets while each trailer vehicle carries six permanent magnets. In accordance with one embodiment, the four permanent magnets on the tractor vehicle can be vertically displaceable independently. In accordance with other embodiments, multiple magnets on the tractor vehicle may be grouped together and actuated by a single motor to form a magnetic coupling unit. In additional embodiments, a tractor vehicle may have multiple, independently controlled magnetic coupling units, e.g., magnet groups 1 and 2 shown in FIG. 5. In one implementation, the tractor vehicle carries eight magnets in two groups of four, the respective groups of four magnets being vertically displaceable independently. Apparatus for implementing this configuration will be described later with reference to FIGS. 6 and 7.

In practice, the minimal number of permanent magnets required for a workable three-vehicle system is two for the tractor vehicle and two for each trailer vehicle. For example, on the horizontal magnetic coupling (through the spar) it may be possible to keep two trailers together (one on either side of the spar) with just one magnet in the middle. But two magnets would still be needed on the tractor vehicle and one on each trailer for the vertical magnetic coupling to make a fully connected system. This would be a total of six magnets for a three-vehicle setup.

Figure 5:
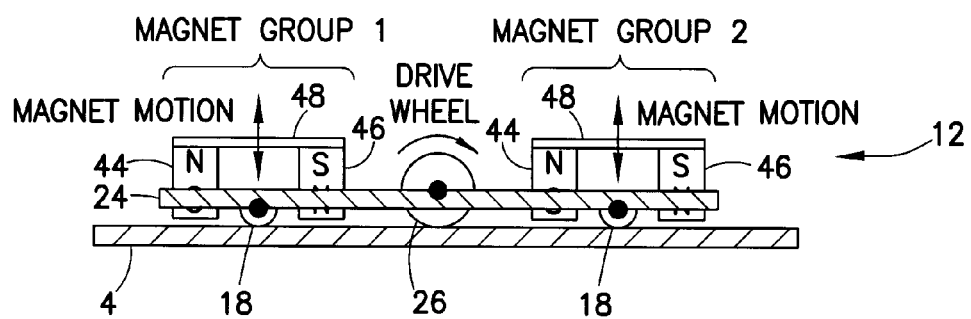
FIG. 5 is a diagram showing a side view of a tractor in accordance with an alternative embodiment.

In accordance with the embodiment depicted in FIG. 5, the tractor vehicle 12 carries two rectangular arrays of four permanent magnets each. Only two magnets from each group are shown in FIG. 5. Each of the magnet pairs comprises a pair of permanent magnets 44 and 46 which are electromagnetically coupled by a respective plate 48 made of ferromagnetic metallic alloy, which serves as a magnet keeper to connect the magnetic circuit between the two permanent magnets 44 and 46. Within each pair, permanent magnet 44 is carried with its North pole up, while permanent magnet 46 is carried with its North pole down. Each plate 48 couples these opposite poles. This alternating North-South arrangement improves the magnetic holding strength of the system compared to a system without connecting plates 48.

Figure 6:
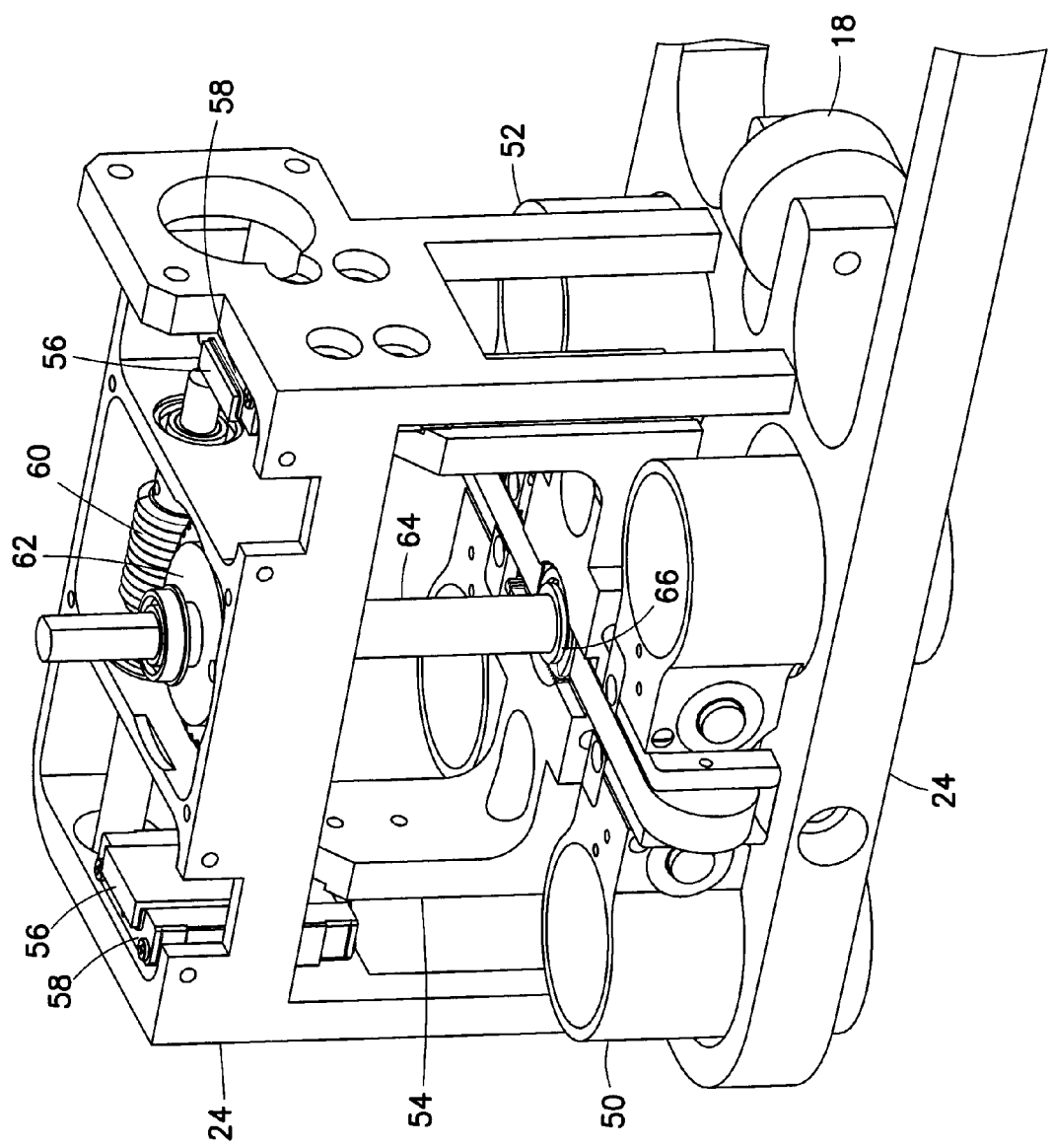
FIGS. 6 and 7 are diagrams showing isometric views of a tractor-mounted magnet carriage that can be raised or lowered as a function of the distance separating the tractor-mounted magnets from opposing trailer-mounted magnets in accordance with one embodiment.
Figure 7:
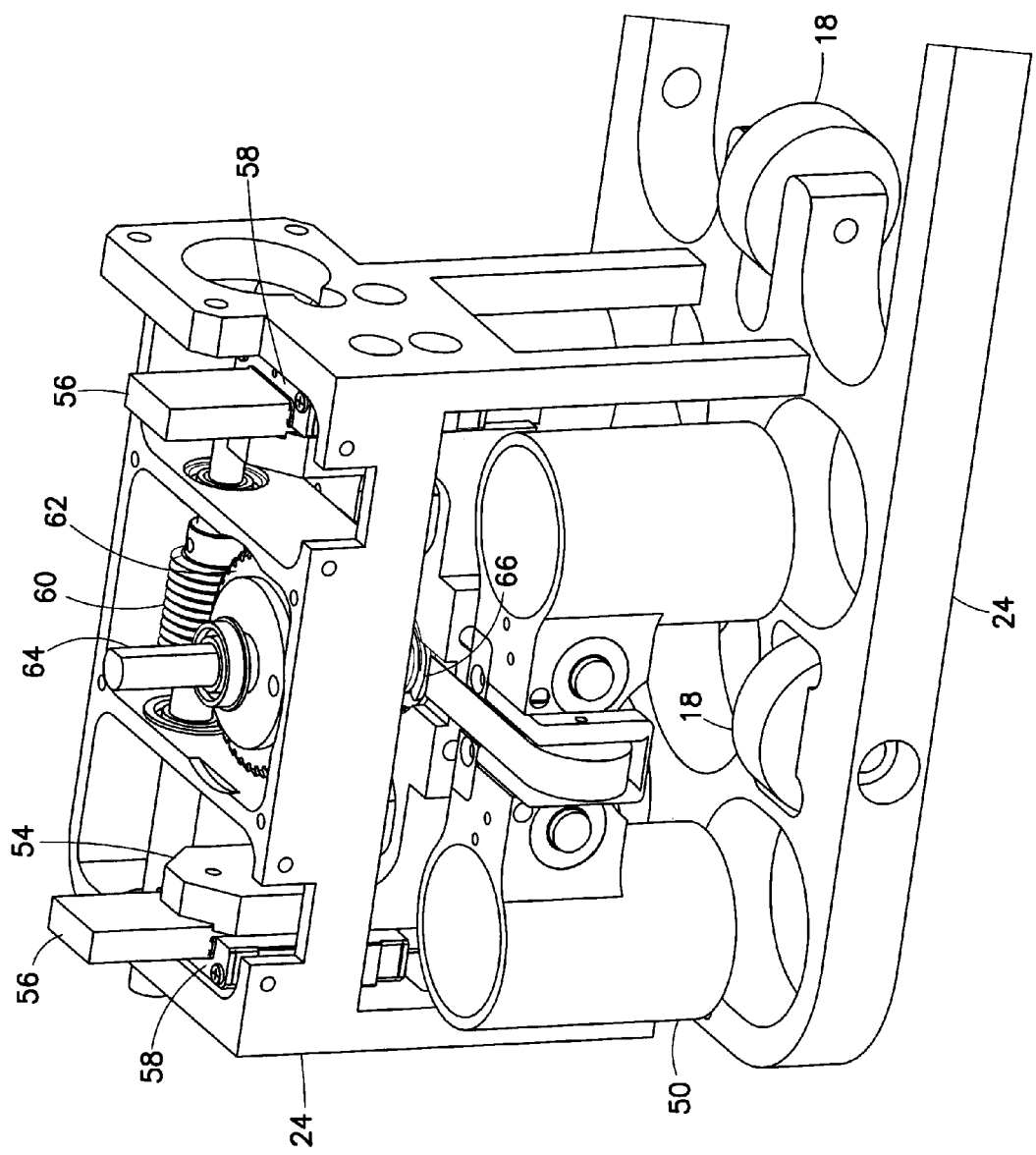

The hardware elements of the adjustable magnetic coupling system on the tractor vehicle include magnets, support structure (e.g., a rigid frame), and motion actuation components. The permanent magnets may be rare earth neodymium permanent magnets, but other types of permanent magnets, electro-magnets, or electro-permanent magnets may also be used. Rare earth magnets can generate a high amount of force when pairs of the magnets are in close proximity to each other, which requires that the containment structure and motion actuators (i.e., stepper motors) be strong enough to overcome the attraction forces that will be generated during operation. FIGS. 6 and 7 show a design for magnet containment structure and motion transmission implementation in accordance with one embodiment.

FIGS. 6 and 7 shows isometric views of a tractor-mounted magnet carriage that can be raised or lowered as a function of the distance separating the tractor-mounted magnets from opposing trailer-mounted magnets in accordance with one embodiment. FIG. 6 shows the magnet carriage in an extended position; FIG. 7 shows the magnet carriage in a retracted position. Actuator motors and permanent magnets are not shown.

Referring to FIG. 6, the magnet carriage comprises two magnet trolleys 50 and 52 mounted to a yoke 54, each trolley being designed to carry a respective pair of magnets (not shown). The yoke 54 has a pair of vertical arms to which respective linear sliders 56 are attached. Each linear slider 56 slides up or down in a respective linear guide 58. The linear guides 58 are attached to upper portions of the frame 24. Each linear guide comprises a linear groove, while each linear slide comprises a bar that fits inside a respective linear groove. Thus the entire magnet carriage can be translated up or down relative to frame 24, thereby raising or lowering all of the magnets carried by the magnet carriage. The vertical position of this magnet group may be a function of the skin thickness at the midpoint between leading and trailing magnets of a magnet group or it may be a function of some other suitable parameter. For example, the algorithm can be altered to set the thickness value for the magnet group based on the position of a specific magnet (or any other position).

The magnet carriage seen in FIG. 6 can be raised or lowered by a vertical displacement transmission subsystem comprising the following elements: a rotatable worm gear 60 coupled to the output of a stepper motor (not shown), a rotatable spur gear 62 threadably coupled to worm gear 60; a rotatable vertical lead screw 64 fixedly attached to spur gear 62 for rotation therewith and having a threaded lower portion (threads not shown in FIG. 6); and a nut 66 threadably coupled to the threaded lower portion of lead screw 64 and fixedly attached to yoke 54. Thus yoke 54 can be raised or lowered by driving worm gear 60 to rotate in one direction or the other, which in turn causes lead screw 64 to rotate. The threaded lower portion of lead screw 64 than causes nut 66 to ascend or descend, thereby raising or lowering yoke 54 to which nut 66 is affixed. FIG. 7 shows the yoke in its raised position, which corresponds to the tractor magnets being in a retracted position relative to opposing trailer magnets.

In accordance with one implementation, the threads on the lead screw 64 and nut 66 have a sufficiently tight pitch that the tractor magnet movement system as a whole is non-backdrivable, meaning that the tractor magnets will not move by themselves when power is cut. This is an important safety feature.

The above-described design is intended to be used with different types of trailer vehicles, which may carry different types of NDI sensor payloads. The main requirements for magnetic coupling from the trailer design perspective are that the magnet spacing pattern should match the spacing of the magnets on the tractor vehicle, and the magnet poles used on the trailer vehicle need to be the opposite of those on the tractor vehicle. Since only the magnets on the tractor vehicle will be moved to control magnet separation distance, the trailer magnets may be in a fixed configuration relative to the trailer structure.

A feedback sensor is needed to provide information required by the control system to adjust the magnet separation distance as the skin thickness varies. One sensor option is a wheel rotation encoder rotatably mounted to the frame of one of the trailer vehicles to provide displacement from a specified starting point along the length of the horizontal stabilizer (or other structure being inspected). This position information, along with predetermined data about the thickness of the skin (either from a CAD model or measured directly), can be used to determine the amount of displacement needed for the movable magnet units on the tractor. By knowing the relative locations of each of the magnetic coupling units to the location of the sensor, the desired separation at each of the magnets can be determined. Alternatively, the encoder could be mounted to the tractor vehicle. However, for NDI applications, it is preferable (from the standpoint of data collection) that the encoder be mounted to the same structure as the NDI scanning unit. This is because there is a small amount of oscillation between the tractor and trailer units through the magnetic coupling.

Figure 8:
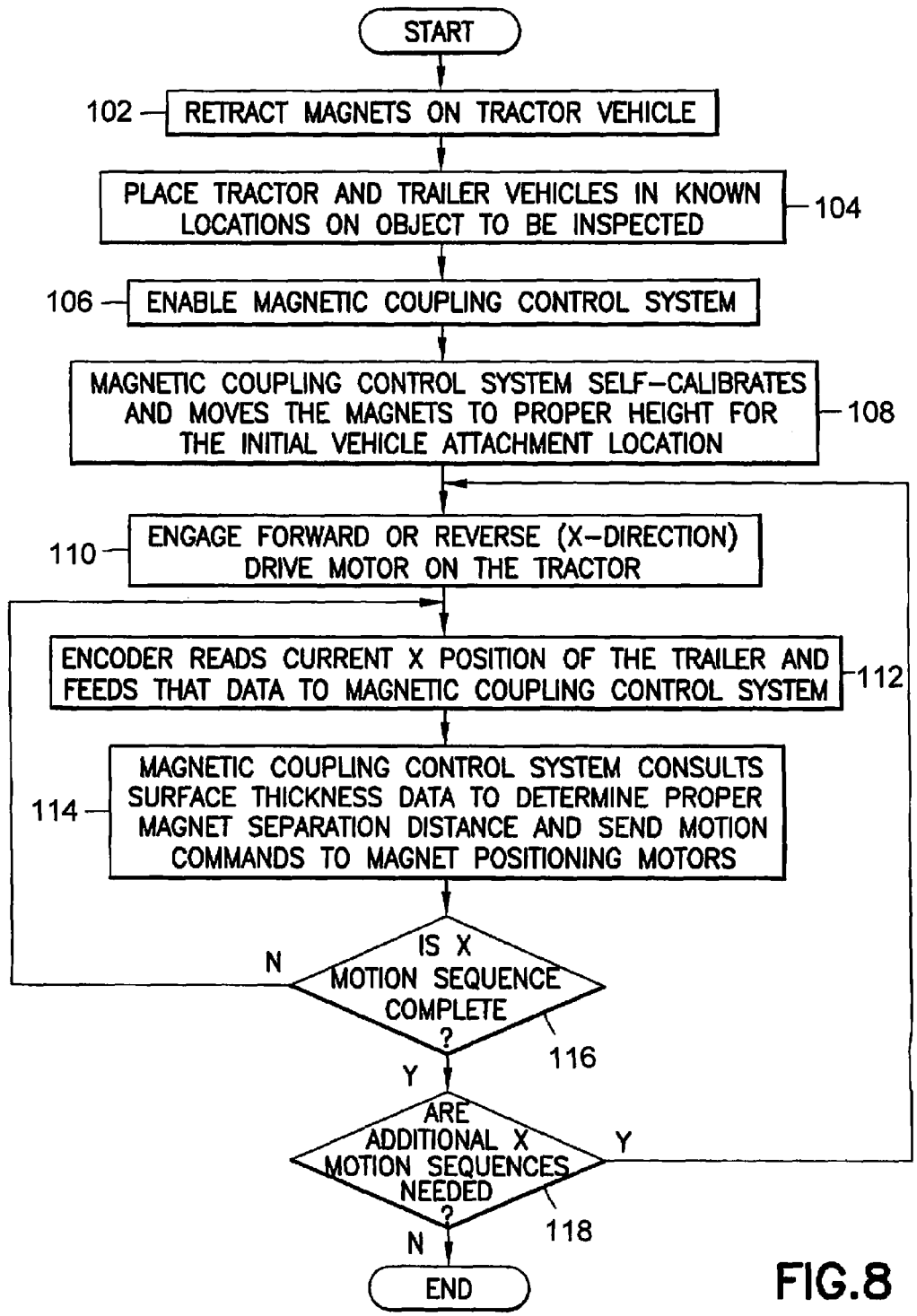
FIG. 8 is a flow chart showing operations performed during a process of adjusting the separation of attraction magnets used to couple trailer and tractor vehicles in accordance with one embodiment.

A process for operation of a system using a trailer-mounted wheel rotation encoder is shown in FIG. 8. Initially, the magnets on the tractor vehicle are retracted (operation 102). Then the tractor and trailer vehicles must be placed in known locations on opposing sides of a top or bottom skin of the object to be inspected (operation 104). This is done by first placing either the tractor vehicle (or the pair of trailer vehicles) in a non-inverted position on the upper surface of a skin and then placing the trailer vehicles (or the tractor vehicle) in an inverted position at a location such that the permanent magnets on the tractor vehicle are aligned with the magnets on the trailer vehicles. Next the magnetic coupling control system is enabled (operation 106). The magnetic coupling control system self-calibrates and sends appropriate motion commands to the magnet vertical positioning motors on the tractor vehicle to move the tractor magnets to the proper height for the initial vehicle attachment location (operation 108). More specifically, the vertical positions of the tractor magnets are adjusted to ensure that the resulting total attraction force is sufficient to support the weight of the inverted vehicle(s) with a margin for safety, but not so great as to cause damage to the intervening skin during vehicle travel. To start the inspection, the motor that drives the drive wheel of the tractor vehicle is engaged by the operator and directed to move in a specific direction and speed by the motion control system. This drive motor can cause the drive wheel to rotate in either direction depending on whether the tractor vehicle will be moving in a forward or reverse direction (operation 110). The resulting line of travel will be referred to herein as the X direction. The magnetically coupled trailer vehicles are pulled in the same direction as the tractor vehicle moves. As the tractor and trailer vehicles move in the X direction, the trailer-mounted wheel rotation encoder reads the current X position of the trailer and feeds that data to the magnetic coupling control system (operation 112). The magnetic coupling control system then consults a surface thickness database to determine the proper magnet separation distance and sends appropriate motion commands to the magnet vertical positioning motors on the tractor vehicle to maintain the separation distance between tractor and trailer magnets within a desired range (operation 114). As the vehicles continue to move in the X direction, the magnetic coupling control system determines, based on feedback from the wheel rotation encoder, whether the X motion sequence has been completed (operation 116 in FIG. 8). If "No", then operations 112, 114 and 116 are repeated. If "Yes", then a determination is made whether additional X motion sequences are needed (operation 118) or not. If "Yes", then operations 110, 112, 114, 116 and 118 are repeated with the vehicles traveling in the opposite direction. If "No", then the process terminates.

Figure 9:
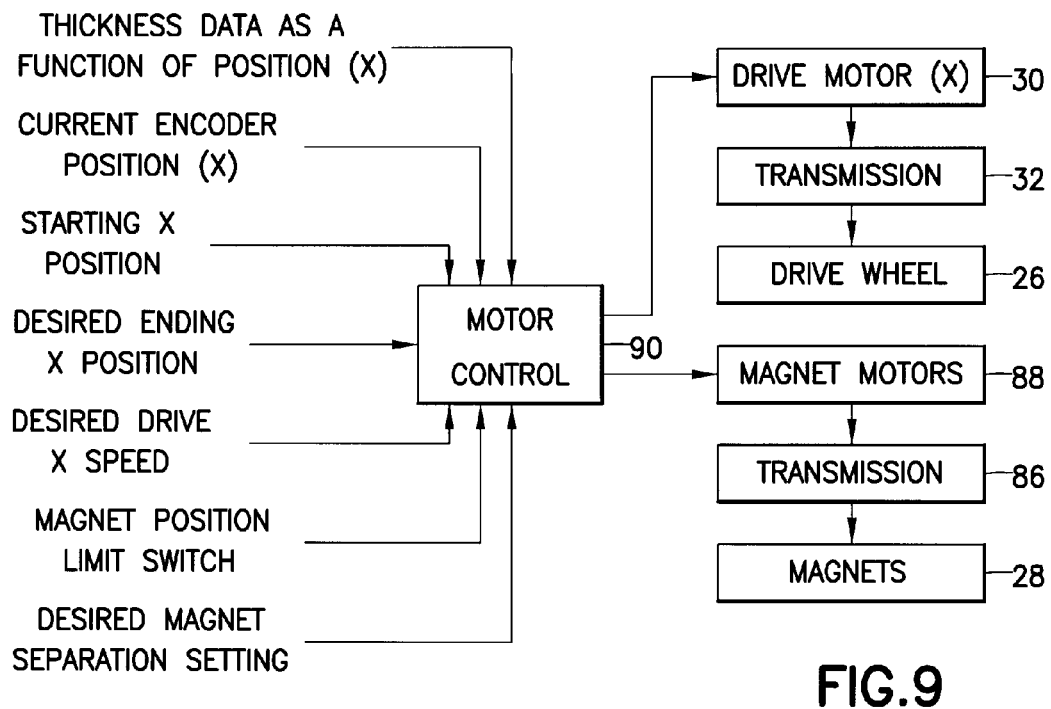
FIG. 9 is a block diagram showing a motor control system in accordance with one embodiment in which a wheel rotation encoder provides trailer position information.

Referring to FIG. 9, the magnetic coupling control system for performing the above-described process comprises a ground-based motor controller 90 that is connected to the tractor vehicle by a flexible electrical cable. This motor controller 90 may comprise a general-purpose computer programmed with respective software modules for controlling magnet vertical positioning motors 88 and drive motor 30. The magnet motors 88 displace the tractor magnets 28 by means of a transmission 86 consisting of the above-described worm drive (worm gear 60 and spur gear 62) for the first stage and the above-described lead screw assembly (lead screw 64 and nut 66) for the second stage. The drive motor 30 drives the drive wheel 26 by means of a transmission 32 that is conventional and well known.

Multiple inputs to the motor controller 90 are shown in FIG. 9. The drive motor 30 is controlled in dependence on a starting X position, a current encoder X position, a desired tractor speed in the X direction, and a desired ending X position. Each magnet motor 88 is controlled in dependence on skin thickness data, a desired magnet separation setting and an output from one or more magnet position limit switches.

The skin thickness is a known function of X. The thickness of the skin can measured directly using instruments like a caliper or micrometer in the areas on the horizontal stabilizer that can be reached (such as around the edges). Ultrasonic or other scanning techniques can also be used to measure thickness. Skin thickness can also be determined using three-dimensional CAD models of the part if available. The data from the three-dimensional part is stored in a file referenced by Cartesian position and used at run time to get the skin thickness at the current position of the tractor-trailer system. These measurement approaches can be performed off-line and the results can be stored in a look-up table or formulated into an equation that is solved at run time.

Limit switches may be included to set the upper or lower limits on magnet motion, and compression springs (not shown) may be included at the lower range to assist in lifting the magnets. Although the motor controller 90 knows how far down the magnets can move before they contact the inspected surface, if the magnets are allowed to reach the surface, the vertical magnet motion mechanism will eventually lift the wheels of the tractor vehicle off the surface, which acts as a type of parking brake (with no harm done to the surface or the tractor vehicle).

To regulate the separation distance of the magnets so that the desired coupling force is produced, a feedback control system is used. In accordance with one embodiment, the motor controller 90 may be a proportional feedback controller. A proportional feedback controller is a type of closed-loop feedback control system in which the input set point for the variable being controlled is a function of the measured value of the output for the same variable. In a typical linear system, the measured variable is multiplied by a feedback gain (K). For example:

$$X\_input = K * X\_output$$

Other forms of feedback control could be used.

The motor controller is programmed to execute operations of an algorithm which causes confronting magnet units to be separated by a distance which is a function of skin thickness. The approach is to maintain a desired separation distance. Since magnetic attraction is inversely proportional to the square of the distance between the magnets, by knowing separation distance, the attraction force can be determined. Using this information and testing, the separation needed to maintain sufficient coupling can be determined using the position control approach. As the vehicles are moving, the control algorithm subtracts the part thickness at the current location from the desired separation distance to determine the distance that the tractor magnets will need to be moved in order to maintain the desired separation. The control algorithm sends a move command to the actuator (magnet motors 88 in FIG. 9) to reduce the difference between the current separation and the desired separation to zero.

An alternate approach to using thickness data at the current location of the vehicles is to measure the force generated by the magnetic coupling using a force sensor, and then increase or decrease the spacing of the magnets to achieve the desired amount of force. For example, a force sensor could be installed between a tractor magnet and the trolley that carries that tractor magnet, to measure the attraction force between that tractor magnet and a confronting magnet on a trailer vehicle. In this configuration, the force data from the force sensor would be part of a closed-loop feedback system that automatically maintains the desired amount of magnetic coupling force by either extending or retracting the tractor magnets. A method based on force sensors would be useful in situations where thickness measurement data is not available.

Figure 10:
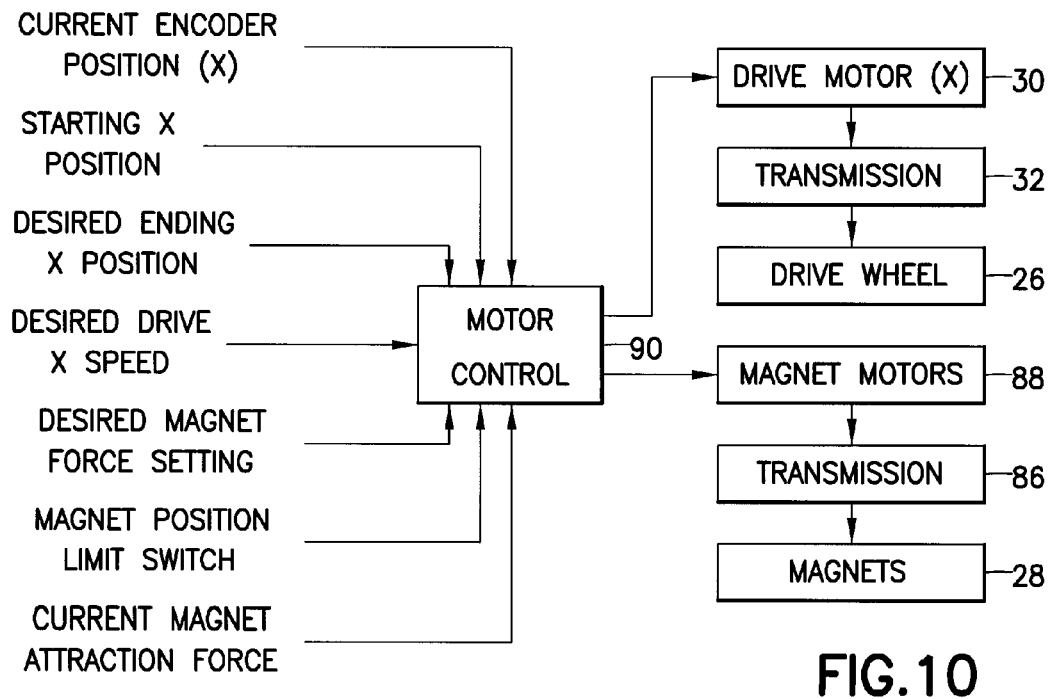
FIG. 10 is a block diagram showing a motor control system in accordance with another embodiment in which a force sensor provides attraction force information.

FIG. 10 shows components of a magnetic coupling control system that utilizes force sensor data to maintain the magnet separation distance within a preset range. In accordance with this embodiment, each magnet motor 88 is controlled in dependence on the difference between the current (measured) magnet attraction force and the desired magnet force setting.

Figure 11:
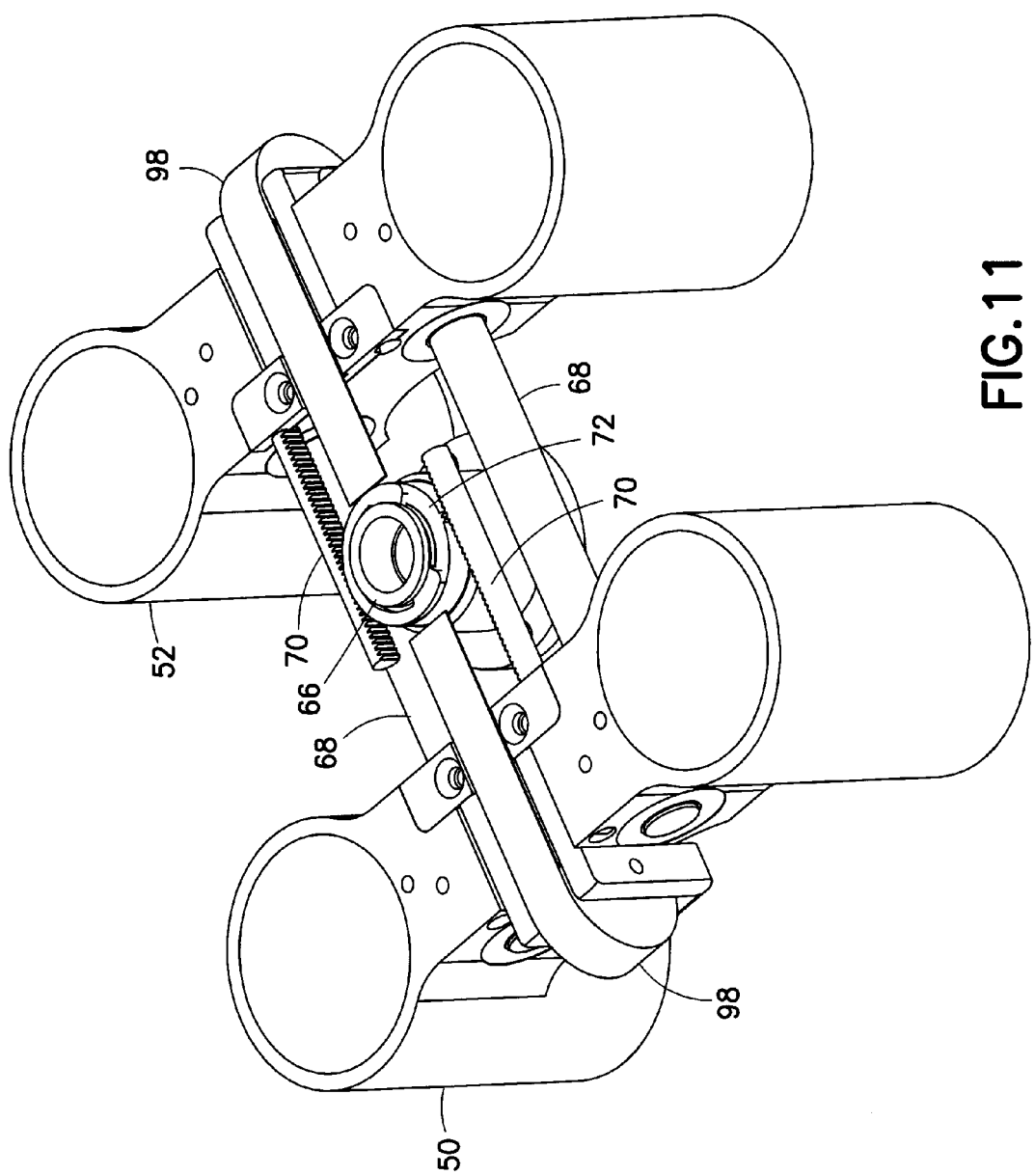
FIG. 11 is a diagram showing an isometric view of a magnet carriage having a lateral separation motion guidance mechanism for magnets on a tractor in accordance with a further embodiment.
Figure 12:
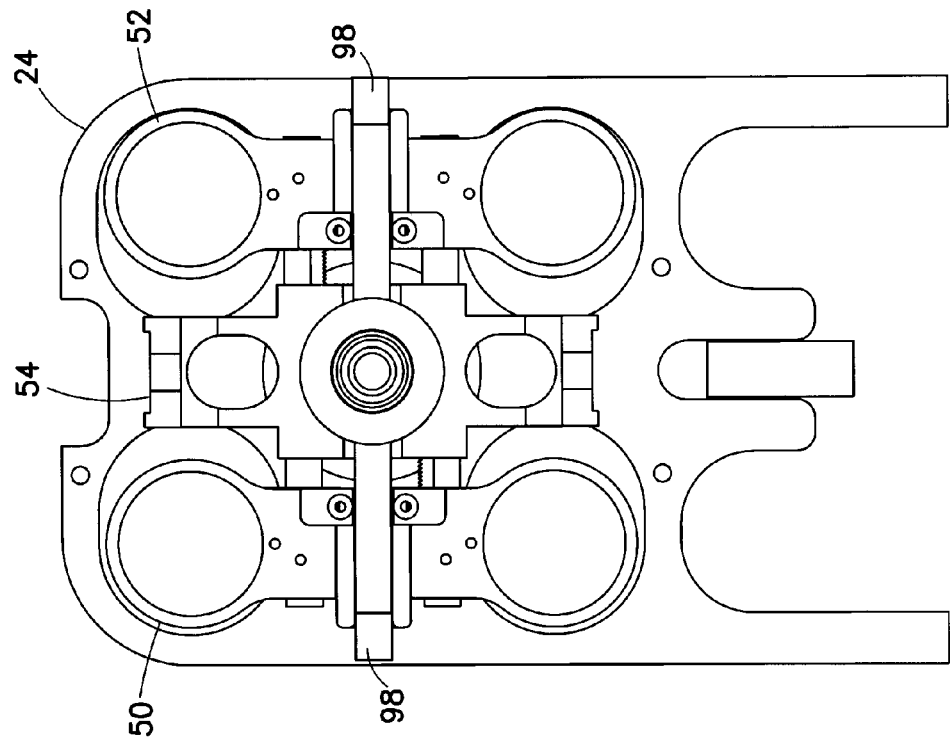
FIGS. 12 and 13 are diagrams showing top views of a portion of a tractor that incorporates the lateral separation motion guidance mechanism shown in FIG. 11.
Figure 13:
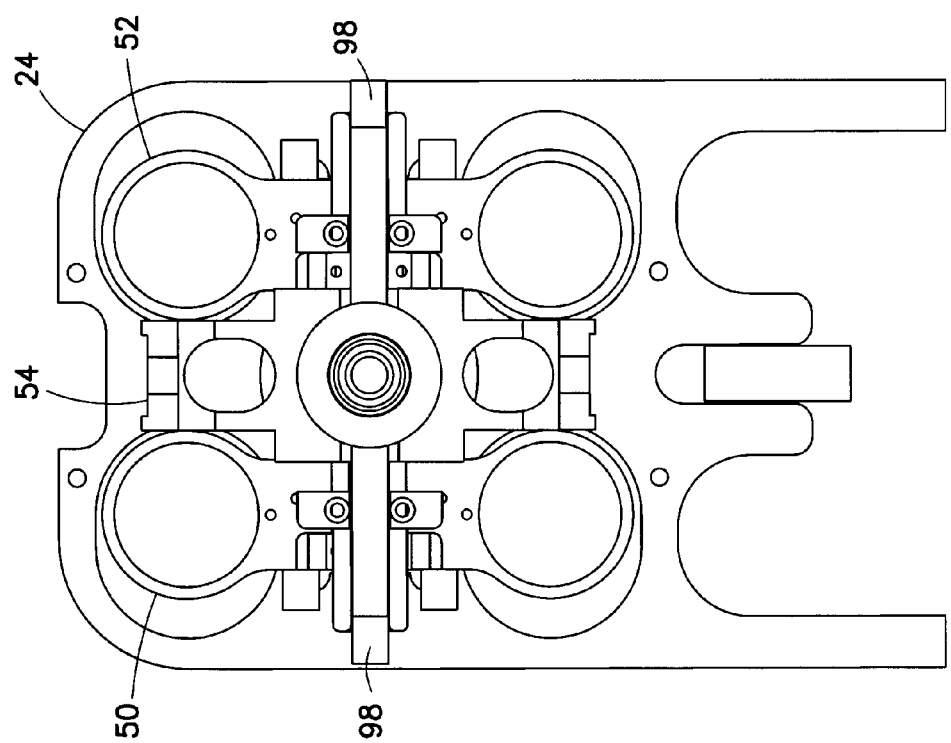

In accordance with a further (optional) feature, the lateral distance separating the tractor magnets can adjust to compensate for variable thickness of the horizontal stabilizer web structure (i.e., spar 8 in FIG. 3). This is in addition to the active magnet control for the variable thickness of the surface skin described above. One embodiment of this lateral separation motion guidance mechanism is shown in FIGS. 11-13. Note that this optional lateral motion capability is independent of the active magnet separation control for the skin (which will function either with or without this enhancement).

As seen in FIG. 11, magnet trolleys 50 and 52 are slidably mounted on a pair of linear cylindrical rails 68 which extend laterally relative to the direction of tractor travel (and laterally relative to the spar of the horizontal stabilizer.) The magnet trolleys are freely slidable along the rails 68 except for spring resistance provided by respective passive springs 98. As the web thickness varies, the changing lateral separation of the corresponding magnetically coupled magnets (i.e., magnets 36 seen in FIG. 3) on the respective trailer vehicles will cause the corresponding tractor magnets (i.e., magnets 28 in seen in FIG. 3) to move laterally toward or away from each other. The passive springs 98 damp oscillations in this lateral magnet movement.

As seen in FIG. 11, a respective rack 70 extends laterally from each magnet trolley. The teeth of racks 70 engage teeth on the outer periphery of a pinion 72. The pinion 72 surrounds the lead screw (not shown). The racks 70 always cause lateral translation of both magnet trolleys in opposite directions. The lateral movement of the tractor magnets (not shown) is guided by the cylindrical rails 68 with the rack and pinion elements providing a way to make sure that the motion is always symmetric on either side of the center.

In accordance with a further (optional) feature, the system controller may be programmed to execute a subroutine for guiding the lateral separation of the pairs of tractor magnets to compensate for variable thickness of the horizontal stabilizer web structure (i.e., spar 8 in FIG. 3). If active control (with motor actuators) is used, the process will be identical to the process for the magnetic coupling through the outer skin surfaces, but using web (spar) thickness and encoder position data as feedback to the motor control algorithm. This process would involve powered rotation of the pinion to directly control the lateral spacing. This can be implemented in several ways. One way is to provide a dedicated actuator (such as an electric motor) to turn the pinion, which drives rack components in or out—independently of the vertical motion. A second way is to drive the pinion with the same motor that is used to move the magnets up and down on the lead screw. With this design there will be one motor simultaneously moving the magnets vertically downward while moving them horizontally outward (and in the reverse direction: upward and inward). The latter arrangement could be utilized if the ratio between the thickness of the skin and the thickness of the spar is relatively consistent.

FIG. 12 shows the magnet trolleys 50 and 52 in a state wherein the lateral magnet separation distance is at an inner limit; FIG. 13 shows the magnet trolleys 50 and 52 in a state wherein the lateral magnet separation distance is at an outer limit.

In accordance with alternative embodiments of a tractor vehicle, electro-magnets or electro-permanent magnets may be used instead of permanent magnets. In such embodiments, the electro-magnets or electro-permanent magnets would not be movable relative to the tractor vehicle frame. Instead of controlling magnet motors to adjust the magnet separation distance, the feedback controller could control the strength of the magnetic field supplied by the electro-magnets or electro-permanent magnets in order to vary the attraction force between it and an opposing permanent magnet of a trailer vehicle.

For embodiments using electro-magnets, coupling force would be controlled by varying the electrical power supplied to the magnets.

In accordance with a further alternative embodiment, permanent magnets on a trailer vehicle could be magnetically coupled to respective arrays of separately controlled electro-permanent magnets on the tractor vehicle. Different magnitudes of attraction force (in discrete increments) can be produced by selectively turning on one or more of the electro-permanent magnets in each array. This would give a discrete number of field strength selections instead of a continuous range. This concept is shown in FIGS. 14-17.

Figure 14:
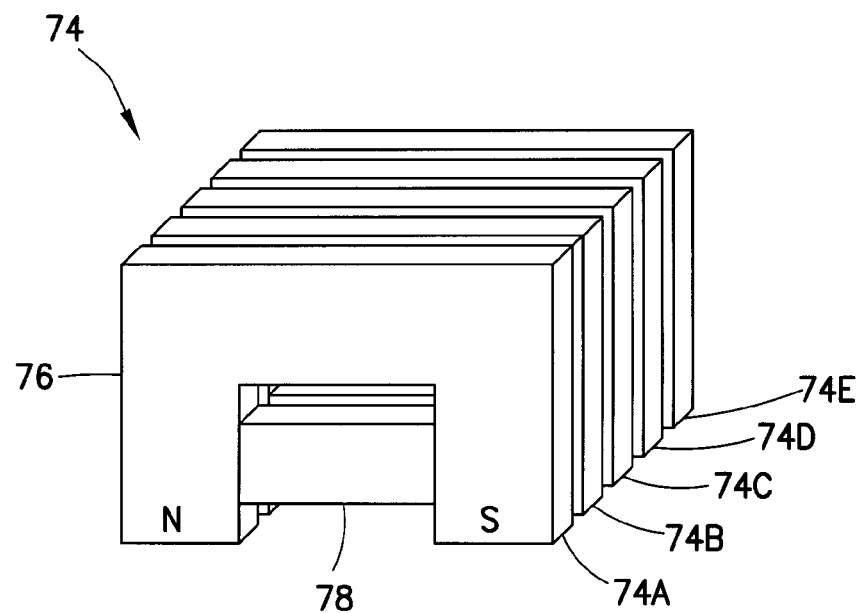
FIG. 14 is a diagram showing an isometric view of an array of electro-permanent magnets suitable for mounting on a tractor vehicle for magnetic coupling with an opposing permanent magnet on a trailer vehicle in accordance with an alternative embodiment.
Figure 15:
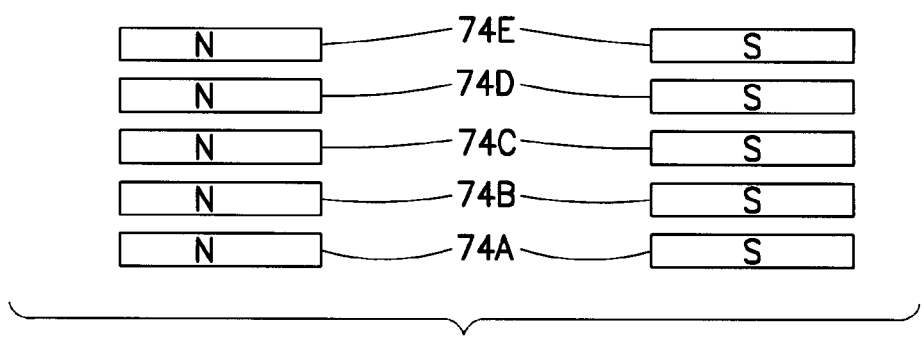
FIG. 15 is a diagram showing a bottom view of the North-South poles of the array of electro-permanent magnets depicted in FIG. 14.

One such array 74 of five electro-permanent magnets 74A-74E is shown in FIG. 14. Each electro-permanent magnet comprises a permanent magnet 76 having North and South poles and a reversible electromagnet 78. The coil of electro-magnet 78 is not shown. This array 74 will be magnetically coupled to one or more permanent magnets on one of the trailer vehicles, which magnet(s) has South and North poles respectively magnetically coupled to the North and South poles of electro-permanent magnets 74A-74E shown in FIG. 15. In this specific case where each array has five electro-permanent magnets, five different magnitudes of attraction force can be produced by selectively turning on one (e.g., 74C), two (e.g., 74B and 74D), three (e.g., 74B-74D), four (e.g., 74A, 74B, 74D and 74E) or five (e.g., 74A-74E) electro-permanent magnets. Individual electro-permanent magnet units with differing strengths could be used in an array in order to produce additional variations.

Electro-permanent magnets are solid-state devices that have zero static power consumption (like permanent magnets), but can be switched on and off like electromagnets. The power only needs to be applied for a brief moment to toggle the state to either on or off, which makes it more useful for applications where overall power usage is preferably low. The use of electro-permanent magnets also has the benefit that, if power is lost, the coupling is still active. The electro-permanent magnet approach requires an electrical power source, but it would only need to be energized for a brief moment to switch the magnetic field state.

Figure 16:
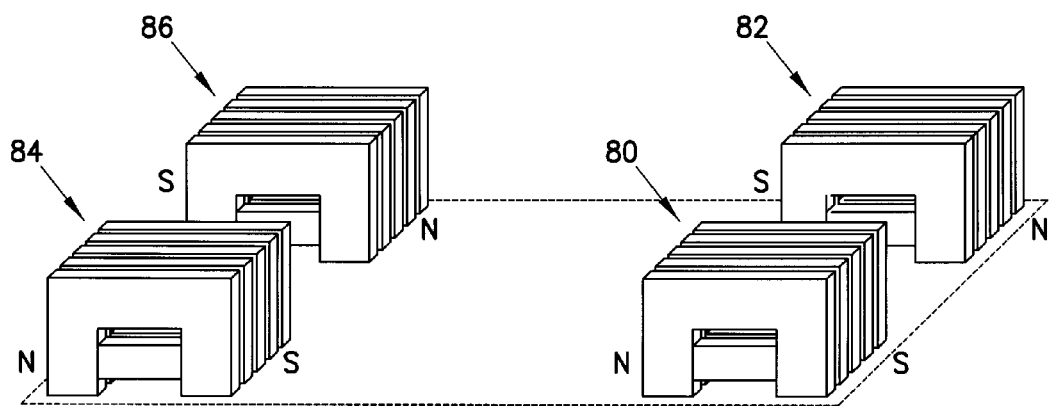
FIG. 16 is a diagram showing an isometric view of multiple arrays of electro-permanent magnets suitable for mounting on a tractor vehicle for magnetic coupling with opposing permanent magnets on two trailer vehicles in accordance with a further embodiment.
Figure 17:
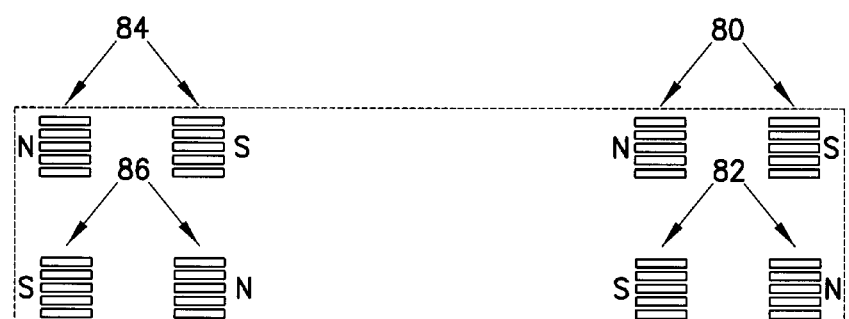
FIG. 17 is a diagram showing a bottom view of the North-South poles of the multiple arrays of electro-permanent magnets depicted in FIG. 16.

FIGS. 16 and 17 show an arrangement of four arrays 80, 82, 84 and 84 of electro-permanent magnets, which can be mounted on the tractor vehicle. Assuming that the tractor vehicle on which these arrays are mounted moves leftward or rightward in the frame of reference of FIG. 16, arrays 80 and 84 would be magnetically coupled to opposing permanent magnets mounted on one trailer vehicle, while arrays 82 and 86 would be magnetically coupled to opposing permanent magnets mounted on the other trailer vehicle.

Figure 18:
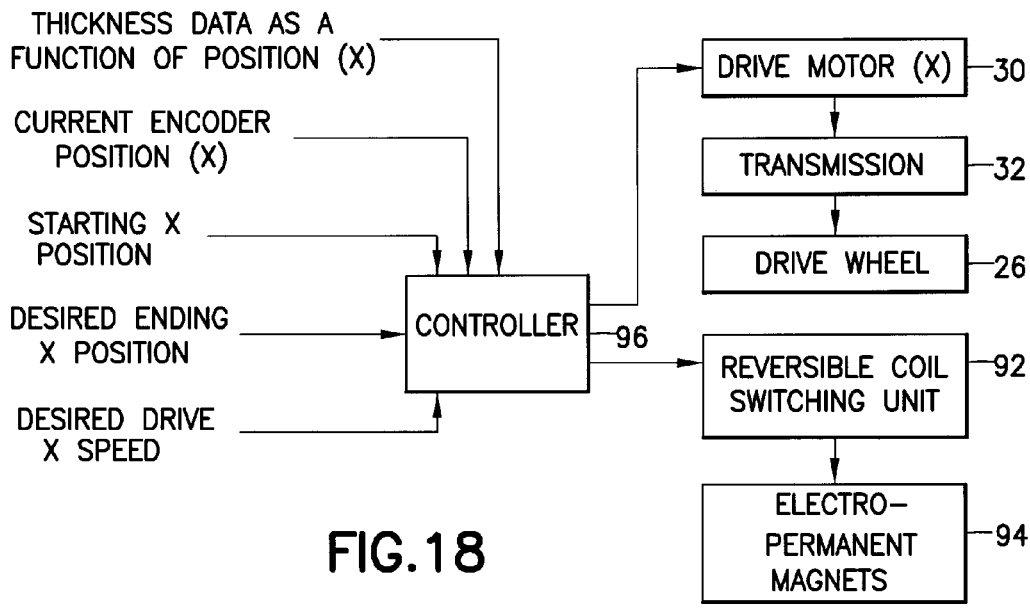
FIG. 18 is a block diagram showing a magnet control system for an electro-permanent magnet array that uses location and thickness data in accordance with a further embodiment.

In accordance with one embodiment partly represented in FIG. 18, the electro-magnet coils of individual electro-permanent magnets are selectively connected to a power source by a magnet controller 96, the selection process being a function of the skin thickness at a particular location as determined from the output of a wheel rotation encoder mounted to a trailer vehicle, as shown in FIG. 18. The controller 96 sends control signals to a reversible coil switching unit 92, which control signals are a function of the current encoder position (X), the thickness data as a function of X position, starting X position, desired ending X position and desired drive X speed. The reversible coil switching unit 92 activates selected electro-permanent magnets 94 in response to control signals from the controller 96. To activate electro-permanent magnet, a momentary pulse in one direction is used. Another pulse with the current flowing in the opposite direction is used to disable the electro-permanent magnet. The rest of the time, there is no electrical power being consumed.

Figure 19:
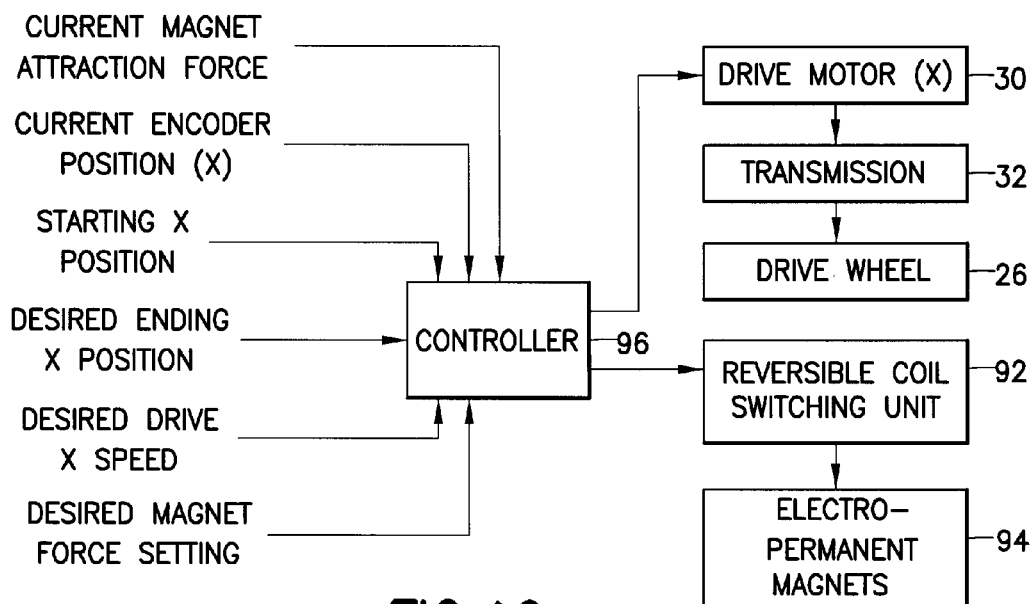
FIG. 19 is a block diagram showing a magnet control system for an electro-permanent magnet array that uses force data in accordance with a further embodiment.

Alternatively, the selection process could be a function of current magnet attraction force data provided by one or more force sensors, as shown in FIG. 19. The control signals from controller 96 are additionally a function of current encoder position (X), starting X position, desired ending X position, desired drive X speed and desired magnet force setting.

The above-disclosed embodiments can be used to inspect the spar surfaces and the filleted join regions between each spar and top and bottom skins, whereas the top and bottom skins are inspected by a different system. Alternatively, it may be possible to inspect the top and bottom skins with a variation of the magnetic coupling concepts disclosed herein. This would involve building a new mechanism to hold the scanner for horizontal surface operations. In this case, the NDI scanning unit may be attached to the tractor vehicle on the outside of the horizontal stabilizer. The passive trailer vehicles would still be used on the inside to provide magnetic coupling, but the payload (scanner) may be on the tractor vehicle.

The above teachings allow magnetically coupled systems to generate a constant attraction force while moving across surfaces with large variations in surface thickness (which is not possible in systems with static magnet positions). In addition to regulating the attraction force control during operation, the ability to control the positions of the magnets also improves operator safety during installation and removal of the tractor from the horizontal stabilizer. The capability to fully retract the magnets when the system is not in use improves the safety of transportation and storage of the system as well. Furthermore, magnet control is not affected by the presence of water on the inside of the horizontal stabilizer, and when powered off, the system will still provide attraction force.

The above-described embodiments can be utilized in NDI-specific types of inspection, but the active magnet separation control process may have uses in other types of applications as well. In addition to various types of NDI sensors, the payload that the vehicle carries may also include: laser scanners, video cameras, robotic manipulators, paint heads, or harnesses for pulling cables through tunnels or ducting.

Regarding drive motion, only one drive option using a central drive wheel has been disclosed in detail. However, other configurations could also take advantage of the variable attraction force concept, for example, a holonomic platform (such as one using Mecanum wheels) or a stationary platform, such as a variable strength magnetic clamp.

While apparatus has been described with reference to various embodiments, it will be understood by those skilled in the art that various changes may be made and equivalents may be substituted for elements thereof. In addition, many modifications may be made to adapt a particular situation to the teachings without departing from the essential scope thereof. Therefore it is intended that the claims not be limited to the particular embodiments disclosed.

The invention claimed is:

1. A system comprising:
a first frame;
a first plurality of wheels that are rotatably coupled to said first frame;
a drive wheel that is rotatably coupled to said first frame; a transmission coupled to said drive wheel;
a motor for driving rotation of said drive wheel via said transmission;
a first array of electro-permanent magnets carried by said first frame;
a switching unit for selectively activating one or more electro-permanent magnets of said first array in response to control signals; and
a controller for sending said control signals to said switching unit, said controller being programmed to cause said switching unit to activate a first number of electro-permanent magnets of said first array and later activate a second number of electro-permanent magnets of said first array, said first and second numbers being different.

2. The system as recited in claim 1, wherein each electro-permanent magnet of said first array comprises a respective permanent magnet having first and second magnet poles of opposite polarity and a respective reversible electromagnet.

3. The system as recited in claim 1, further comprising: a second frame; a second plurality of wheels that are rotatably coupled to said second frame; a skin made of non-magnetic material having a variable thickness, said skin extending between said first and second frames; and third and fourth magnet poles carried by said second frame and respectively magnetically coupled to respective first and second magnet poles of at least one of said electro-permanent magnets of said first array through said skin.

4. The system as recited in claim 3, wherein said controller is further programmed to cause said switching unit to send a pulse of electrical current to one of said electro-permanent magnets of said first array when an intervening thickness of said skin crosses a specified threshold during tandem movement of said first and second frames, wherein said pulse of electrical current flows in one direction when said one electro-permanent magnet is being activated and flows in an opposite direction when said one electro-permanent magnet is being de-activated.

5. The system as recited in claim 3, wherein said controller is further programmed to cause said switching unit to send a pulse of electrical current to one of said electro-permanent magnets of said first array when the sum of the attraction force between said first and third magnet poles and the attraction force between said second and fourth magnet poles crosses a threshold during tandem movement of said first and second frames, wherein said pulse of electrical current flows in one direction when said one electro-permanent magnet is being activated and flows in an opposite direction when said one electro-permanent magnet is being de-activated.

6. The system as recited in claim 3, further comprising: a second array of electro-permanent magnets carried by said first frame; a third plurality of wheels that are rotatably coupled to said second frame; a third frame disposed on the same side of said skin where said second frame is disposed; fourth and fifth pluralities of wheels that are rotatably coupled to said third frame; a web made of non-magnetic material connected to said skin and having a variable thickness, said web extending between said second and third frames; and fifth and sixth magnet poles carried by said third frame and respectively magnetically coupled to seventh and eighth magnet poles of at least one of said electro-permanent magnets of said second array through said skin.

7. The system as recited in claim 3, further comprising a tool or sensor carried by said second frame.

8. The system as recited in claim 3, further comprising an encoder wheel rotatably coupled to said second frame, said encoder wheel being oriented to encode motion of said second frame in a direction perpendicular to axes of rotation of said second plurality of wheels.

9. The system as recited in claim 8, wherein said controller is further programmed to activate said motor to cause said first frame to travel in a direction parallel to said web based on data representing the encoded motion of said second frame.

10. A tractor vehicle comprising:
a frame;
a plurality of wheels rotatably coupled to said frame;
a drive wheel rotatably coupled to said frame;
a transmission coupled to said drive wheel;
a motor for driving rotation of said drive wheel via said transmission in response to receipt of motor control signals;

first and second arrays of electro-permanent magnets carried by said frame;
a switching unit for selectively activating one or more electro-permanent magnets of said first array and one or more electro-permanent magnets of said second array in response to control signals; and
a controller for sending said control signals to said switching unit, said controller being programmed to cause said switching unit to activate a first number of electro-permanent magnets of said first array and a second number of electro-permanent magnets of said second array when the first and second arrays are different distances from respective other magnets, said first and second numbers of activated electro-permanent magnets being different.

11. The tractor vehicle as recited in claim 10, further comprising third and fourth arrays of electro-permanent magnets carried by said frame, wherein said first through fourth arrays are arranged in respective quadrants of said frame.

12. The tractor vehicle as recited in claim 11, wherein each electro-permanent magnet of said first through fourth arrays comprises a respective permanent magnet having first and second magnet poles of opposite polarity and a respective reversible electromagnet.

13. A method for maintaining a magnetic coupling between at least one activated electro-permanent magnet of an array of electro-permanent magnets onboard a tractor vehicle and first and second permanent magnets onboard a trailer vehicle through an intervening skin having a variable thickness along a vehicle travel path, comprising:
    placing one of the tractor vehicle and the trailer vehicle in a non-inverted position with wheels in contact with a top surface of the skin;
    placing the other of the tractor vehicle and the trailer vehicle in an inverted position with wheels in contact with a bottom surface of the skin and with respective poles of the first and second permanent magnets onboard the trailer vehicle magnetically coupled to respective poles of at least one electro-permanent magnet of the array of electro-permanent magnets onboard the tractor vehicle;
    driving the tractor vehicle along the vehicle travel path; and
    adjusting the number of electro-permanent magnets of the array which are activated as the tractor vehicle travels along the vehicle travel path, the adjustments to the number of active electro-permanent magnets in the array being such that an attraction force between the array of electro-permanent magnets on the tractor vehicle and the first and second permanent magnets on the trailer vehicle is maintained within a range as the skin thickness varies along the vehicle travel path.

14. The method as recited in claim 13, further comprising mounting a tool or sensor on the trailer vehicle.

15. A method for coupling a tractor vehicle carrying a plurality of arrays of electro-permanent magnets to a trailer vehicle carrying a plurality of permanent magnets through an intervening skin having a variable thickness along a vehicle travel path, comprising:
    placing the tractor vehicle in a non-inverted position with wheels in contact with a top surface of the skin;
    activating one or more electro-permanent magnets of each array of electro-permanent magnets;
    placing the trailer vehicle in an inverted position with wheels in contact with a bottom surface of the skin and with poles of the plurality of permanent magnets respectively magnetically coupled to respective poles of the one or more activated electro-permanent magnets of the plurality of arrays;
    driving the tractor vehicle along the vehicle travel path; and
    adjusting the number of electro-permanent magnets of the plurality of arrays which are activated as the tractor vehicle travels along the vehicle travel path, the adjustments to the number of activated electro-permanent magnets in the arrays being such that the sum of the respective attraction forces between the electro-permanent magnets on the tractor vehicle and the permanent magnets on the trailer vehicle is sufficient to support a weight of the inverted trailer vehicle.

16. A method for coupling a tractor vehicle carrying first and second pluralities of arrays of electro-permanent magnets to first and second trailer vehicles which each carry a respective plurality of permanent magnets through an intervening skin having a variable thickness along a tractor vehicle travel path, comprising:
    placing the first trailer vehicle in a non-inverted position with a first set of wheels in contact with a top surface of the skin and a second set of wheels in contact with one side of a web that is connected to and projects upward from the skin;
    placing the second trailer vehicle in a non-inverted position with a third set of wheels in contact with a top surface of the skin and a fourth set of wheels in contact with the other side of the web;
    activating one or more electro-permanent magnets of each of the first and second pluralities of electro-permanent magnets carried by the tractor vehicle; and
    placing the tractor vehicle in an inverted position with a multiplicity of wheels in contact with a bottom surface of the skin, with poles of the plurality of permanent magnets carried by the first trailer vehicle respectively magnetically coupled to respective poles of the one or more activated electro-permanent magnets of the first plurality of arrays of electro-permanent magnets, and with poles of the plurality of permanent magnets carried by the second trailer vehicle respectively magnetically coupled to respective poles of the one or more activated electro-permanent magnets of the second plurality of arrays of electro-permanent magnets.

17. The method as recited in claim 16, further comprising: driving the tractor vehicle along the vehicle travel path; and adjusting the number of electro-permanent magnets of the first and second pluralities of arrays of electro-permanent magnets which are activated as the tractor vehicle travels along the tractor vehicle travel path, the adjustments being such that the sum of the respective attraction forces between the electro-permanent magnets on the tractor vehicle and the permanent magnets on the first and second trailer vehicles is sufficient to support a weight of the inverted tractor vehicle.

* * * * *